(12) United States Patent
Golenhofen

(10) Patent No.: US 6,233,307 B1
(45) Date of Patent: May 15, 2001

(54) COMPACT X-RAY SPECTROMETER

(75) Inventor: Rainer Golenhofen, Ettlingen (DE)

(73) Assignee: Bruker AXS Analytical X-Ray Systems GmbH, Karlsruhe (DE)

( * ) Notice: Subject to any disclaimer, the term of this patent is extended or adjusted under 35 U.S.C. 154(b) by 0 days.

(21) Appl. No.: 09/298,953

(22) Filed: Apr. 26, 1999

(30) Foreign Application Priority Data

May 7, 1998 (DE) .............................. 198 20 321

(51) Int. Cl.⁷ .................................. G01N 23/223
(52) U.S. Cl. ............................... 378/45; 378/44
(58) Field of Search ...................... 378/45, 44, 46, 378/47, 48, 49, 50, 80, 201

(56) References Cited

U.S. PATENT DOCUMENTS

| | | | |
|---|---|---|---|
| 3,777,124 | * 12/1973 | Pavkovich | 235/151 |
| 4,417,355 | 11/1983 | Anisovich et al. | |
| 5,406,608 | * 4/1995 | Yellepeddi et al. | 378/46 |
| 5,528,647 | * 6/1996 | Anderson et al. | 378/44 |
| 5,712,891 | * 1/1998 | Benony et al. | 378/47 |
| 5,832,054 | * 11/1998 | Kuwabara | 378/45 |
| 5,898,752 | * 4/1999 | Van Der Wall | 378/49 |
| 5,978,442 | * 11/1999 | Kuwabara | 378/46 |

FOREIGN PATENT DOCUMENTS

| | | |
|---|---|---|
| 1984796 U | 8/1967 | (DE) . |
| 1598167 | 3/1971 | (DE) . |
| 4212408A1 | 11/1992 | (DE) . |
| 1219448 | 1/1971 | (GB) . |
| WO 97/05474 | 2/1997 | (WO) . |

OTHER PUBLICATIONS

Company leaflet "Spectrometry Solutions SRS 3400 mit Spectra$^{plus}$" of the company Bruker AXS dated 1997.

* cited by examiner

Primary Examiner—Robert H. Kim
Assistant Examiner—Irakli Kiknadze
(74) Attorney, Agent, or Firm—Paul Vincent

(57) ABSTRACT

An X-ray fluorescence spectrometer (1) for the analysis of a solid or liquid sample (4) arranged in a measuring position on a sample holder (3) in a compact sample chamber (2), the sample having a maximum linear extension of 1 dm, with an X-ray tube (6) projecting into the sample chamber for irradiating the sample and with a detector (13) being arranged in a detector chamber (9), wherein the detector chamber can be separated in a vacuum-tight manner from the sample chamber by means of a closing element (8), is characterized in that the sample chamber comprises a moveable wall element (5) which, in an "open" state, permits direct access to the sample (4) in its measuring position in the sample chamber (2) and, in a "closed" state, seals the sample chamber (2) with respect to the surrounding atmosphere. In this manner, the spectrometer is more compact and fabrication is considerably easier, charging of the sample chamber with a test sample is less demanding, gas exchange between the respective chambers is simplified, the operational safety of the device, in particular during the sample changing phase, is increased and maintenance and repair works of the sample chamber itself are facilitated.

20 Claims, 2 Drawing Sheets

COMPACT X-RAY SPECTROMETER

This application claims Paris Convention priority of German patent application number 198 20 321.7 filed May 7, 1998, the complete disclosure of which is hereby incorporated by reference.

BACKGROUND OF THE INVENTION

The invention relates to an X-ray fluorescence spectrometer for the analysis of a solid or liquid sample disposed in a measuring position inside a compact sample chamber of a volume of $\leq 10$ dm$^3$ preferably <1dm$^3$, on a sample holder. The sample has a maximum linear extension of 1 dm. An X-ray tube is projecting into the sample chamber for irradiating the sample, and a detector is arranged in a detector chamber, wherein the detector chamber can be separated in a vacuum tight manner from the sample chamber by means of a shutter element.

An X-ray fluorescence spectrometer of this type is e.g. known from the device "SRS 3400" described in the company leaflet "SPECTROMETRY SOLUTIONS SRS 3400 mit SPECTRA$^{plus}$" of the company Bruker AXS GmbH dated 1997.

In order to examine the composition of a test sample—in an X-ray fluorescence spectrometer—X-rays are usually irradiated onto a surface of the sample, and the X-ray fluorescence radiation emitted by the sample is detected, the wavelength distribution of which being characteristic for the elements present in the sample, while their intensity distribution—gives information about the relative abundance of the sample components. By means of a spectrum obtained in this manner, the expert is able to determine to a relatively exact extent the components and quantitative proportions of the examined test sample.

During a measurement, the sample is usually held in a fixed measuring position in the sample chamber. If necessary, it can also be rotated. The sample chamber is either evacuated during the measurement or is flooded with an inert gas, usually helium. In order to establish acceptable measuring conditions, the sample chamber must be connected to a suitable pumping system since, during introduction of a new test sample into the sample chamber, air from the surrounding atmosphere enters the sample chamber which must be removed again from this location prior to the actual measurement.

For charging the sample chamber with a test sample and subsequent elimination of incoming atmospheric air, known X-ray fluorescence spectrometers comprise a transfer chamber which can be evacuated and through which the test sample to be examined can be introduced from the outside. In this way, the sample chamber itself is at first disconnected from the outer atmosphere. The transfer chamber is not opened towards the sample chamber until the transfer chamber has been closed and evacuated (or after thorough flushing with inert gas) and the sample can be transferred to its measuring position.

A disadvantage of the known X-ray fluorescence spectrometers is their construction which requires a lot of space owing to the transfer chamber, and also the relatively high production costs for the complicated construction of the transfer chamber and sample chamber system. The mode of operation for this system in which at first the sample chamber has to be vacuum-disconnected from the transfer chamber, and then the transfer chamber has to be subjected to atmospheric pressure, charged with the sample, and subsequently sealed off again from atmosphere and evacuated, whereupon the sample chamber is opened towards the transfer chamber and the sample is transported to its measuring position and subsequently the sample chamber is again sealed off from the transfer chamber and finally subjected to a measuring vacuum or flooded with the corresponding inert gas, is not only very time consuming but also relatively vulnerable to errors occurring during the complicated individual steps.

A further disadvantage consists in that the sample chamber cannot be accessed directly from the outside and therefor the entire system has to be dismounted for any modifications, repairs or maintenance works within the sample chamber which requires a high amount of time and effort.

The fact that the system comprises a transfer chamber and a sample chamber requires also complicated internal transport means for transporting the sample out of the transfer chamber into the measuring position inside the sample chamber which step is also vulnerable to operational errors.

In contrast thereto, it is the object of the present invention to improve an X-ray fluorescence spectrometer of the initially described type in such a manner that its mechanical construction is rendered more compact and considerably simpler such that charging of the sample chamber with a test sample becomes less difficult, that the operational steps of the required gas exchange between the chambers involved are facilitated, that operational safety is increased and that maintenance and repair works on the sample chamber itself are facilitated.

SUMMARY OF THE INVENTION

According to the invention, this object is achieved in a manner which is both, surprisingly easy and effective. The sample chamber comprises a moveable wall element which permits in the "open" state direct access to the sample in its measuring position inside the sample chamber and, in the "closed" state, seals the sample chamber with respect to the surrounding atmosphere. In this manner, the transport chamber provided in known X-ray fluorescence spectrometers may be completely omitted, whereby also the transport devices for positioning the sample in its measuring position can either be disposed of completely or at least considerably facilitated. This increases the operational safety decisively during a sample change. The pumping and gas flushing steps are also considerably facilitated since only one single chamber, i.e. the sample chamber, has to be aired, flooded or evacuated. Owing to the direct access from the outside to the measuring position inside the sample chamber, maintenance, repair or modification works can be carried out in the sample chamber without any problems and without large-scale disassembling of the entire apparatus.

In a particularly preferred embodiment of the inventive X-ray fluorescence spectrometer, the moveable wall element is sliding and/or revolving. In this way, it is possible to realize by means of simple technical means a combined opening and sealing function of the moveable wall element. But also complicated arrangements are feasible wherein the moveable wall element is e.g. screwed on or leak tight fixed in another manner onto a corresponding opening in the sample chamber.

Also preferred is an embodiment in which a sample changing means is provided which cooperates with the moveable wall element, preferably in the form of an automatic sample changing device. In this manner, the operation of the inventive X-ray fluorescence spectrometer can be considerably simplified, high comfort in handling the system is achieved and a quick sequence of routine measurements is possible.

In a preferred further development of this embodiment the sample changing means can always transport the sample to be examined directly from the atmosphere surrounding the sample chamber into the measuring position inside the sample chamber. In this way, charging of the sample chamber with a new test sample is considerably accelerated and less mechanical steps are required to introduce the sample than in prior art systems which contributes to a further improvement of the operational reliability of the inventive X-ray fluorescence spectrometer.

In order to shield the environment from the X-rays generated during operation, the moveable wall element of a preferred embodiment is essentially impervious to the radiation emitted by the X-ray tube.

Preferably, the moveable wall element contains lead, whereby the shielding effect is even further improved.

Particularly preferred are embodiments of the inventive X-ray fluorescence spectrometer where in the "open" state of the moveable wall element direct access is possible from the atmosphere surrounding the sample chamber to an exit window of the X-ray tube, to a primary beam filter element, to the vacuum-tight closing element or also to other components arranged in the sample chamber, whereby maintenance and repair convenience is further enhanced.

A further preferred embodiment comprises an aperture diaphragm arranged in the sample chamber between the measuring position of the sample and the closing element to mask the edge areas of the fluorescent light emitted by the sample. The field of view of a collimator arranged in the detector chamber is thereby limited in such a manner to ensure that it contains only fluorescent light emitting from the sample surface. In this manner, the interfering background is reduced and the signal-to-noise ratio of the spectrometer is further improved.

In an advantageous further development of this embodiment, direct access from the atmosphere, surrounding the sample chamber, to the aperture diaphragm is possible in the "open" state of the moveable wall element, such that the aperture diaphragm can easily be changed or is accessible for fine adjustments without problems.

In a further preferred embodiment of the inventive X-ray fluorescence spectrometer, the vacuum-tight closing element is transparent to X-ray fluorescence radiation over a predetermined wavelength range. In this manner, during a measurement the sample chamber may be flooded also with an inert gas, while the detector chamber can be kept under vacuum.

This can be realized in a simple way by a vacuum-tight closing element in the form of a rigid wall element. If the X-ray transparent closing element is transparent to all interesting analytically relevant wavelengths, it is no longer necessary to physically remove the closing element in order to achieve a sealing effect between sample chamber and detector chamber. In this manner the mechanics of the spectrometer can be produced at considerable lower costs.

Alternatively, in a further embodiment the closing element may be formed as a slide or flap with vacuum-tight closing fit. This permits removal of the closing element during measurements under vacuum whereby the X-ray fluorescence signal reaches the detector chamber directly from the sample surface with higher intensity.

Preferably, the sample chamber can be evacuated such that during a measurement, there is no absorption of the X-ray fluorescence light in a sample chamber gas. In this way also a wider operational wavelength range of the X-ray fluorescence spectrometer is achieved.

In a further preferred embodiment, the sample chamber may be flooded with gas, preferably an inert gas, in particular nitrogen or helium. In this way, it is also possible to carry out measurements with liquid samples, the surface of which would otherwise start to boil in case of evacuation of the sample chamber. By using nitrogen, it is possible to remove interfering gases from the atmosphere of the sample chamber at low costs, while the more expensive helium has an increased transparency for X-ray light.

A preferred embodiment of the inventive X-ray fluorescence spectrometer comprises a detector chamber which can be evacuated. This results in low absorption of the detected X-ray fluorescence light along the beam path, internal intensity fluctuations are avoided and the sensitivity of the detector is increased.

The inventive X-ray fluorescence spectrometer is preferably wave length-dispersive because in this way one can achieve higher resolution and more accurate measurement results in comparison to an energy-dispersive embodiment.

In further improvements of this embodiment, the detector chamber contains a first collimator, an analyzer element, preferably an analyzer crystal, and a second collimator. Prior art X-ray fluorescence spectrometers are usually constructed this way such that already existing technologies, in particular completely equipped detector chambers, can be utilized in combination with the inventive Xray fluorescence spectrometer without requiring larger modifications.

In a sample chamber modified according to the invention the X-ray tube can advantageously illuminate at least half of the sample surface areas facing the X-ray tube with the sample in its measuring position. In this way, simple mechanic means achieve a high yield of detected X-ray fluorescence radiation and an optimum adaptation to standard sample sizes can be realized.

Further advantages of the invention can be gathered from the description and the drawing. The features mentioned above and below may be utilized according to the invention individually or in any arbitrary combination. The embodiments shown and described are not to be understood as exhaustive enumeration but rather have exemplary character for describing the invention.

BRIEF DESCRIPTION OF THE DRAWINGS

The invention is shown in the drawing and is further explained by means of an embodiment. In the drawing.

DETAILED DESCRIPTION OF THE PREFERRED EMBODIMENTS

Figure 1:
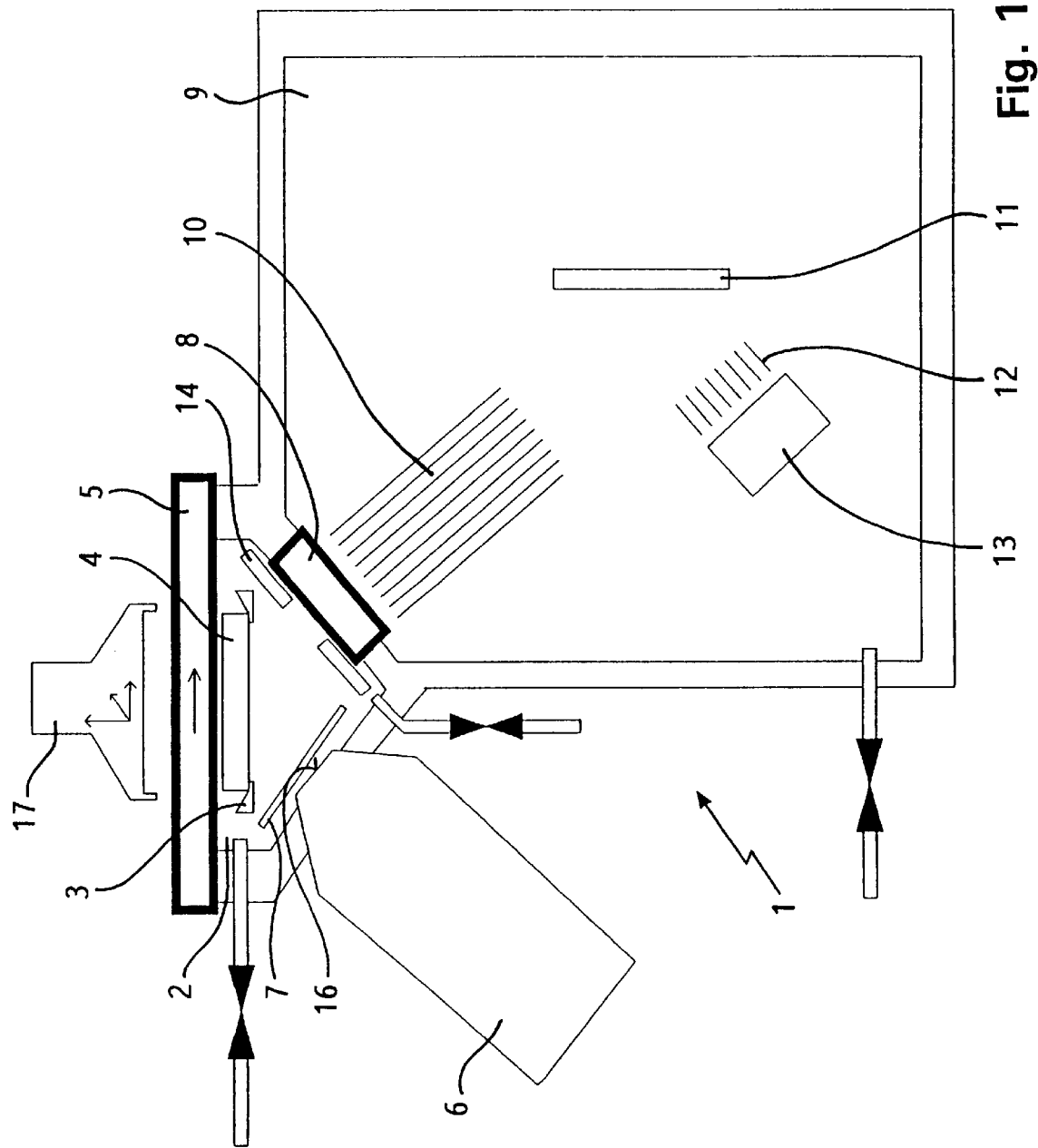
FIG. 1 shows a schematic horizontal cross section through an embodiment of the inventive X-ray fluorescence spectrometer.

The X-ray fluorescence spectrometer 1 according to the invention schematically shown in FIG. 1 comprises a sample chamber 2 with a sample holder 3 for the exact stationary support of a test sample 4 to be examined in its measuring position. The sample 4 may be a compact solid, e.g. a cylinder pressed or sintered from ground rock samples, but also e.g. a liquid disposed in a suitable container, wherein the maximum linear extension of the sample 4 is no greater than 0.1 m. The volume of the compact sample chamber 2 is usually less than 10 $dm^3$, in most cases even less than 1 $dm^3$.

The sample chamber 2 can be evacuated and/or optionally be flooded with an inert gas, in particular with nitrogen or helium. For charging the sample chamber 2 with the test sample 4, the sample chamber 2 comprises a moveable wall element 5 which, in the "open" state, allows direct access to the sample 4 in its measuring position inside the sample chamber 2 and in the "closed" state, seals the sample chamber 2 with respect to the surrounding atmosphere. In order to open the sample chamber 2, the moveable wall element 5 may be formed such that it is sliding and/or revolving. However, it may also be disposed on the corresponding opening of the sample chamber 2 in any alternative sealing manner.

An X-ray tube 6 projects into the sample chamber 2, the X-ray radiation of which, emerging from an exit window 16, can be spectrally hardened by means of a primary beam filter element 7 before reaching the surface of the sample 4. The X-ray tube 6 is arranged in relation to the sample 4 in its measuring position in the sample support 3 such that at least half of the surface area of the sample 4 facing the exit widow 16 is illuminated.

Part of the X-ray fluorescence light emitted by the sample surface reaches a detector chamber 9 through a closing element 8 which is transparent to the X-ray fluorescence radiation emitted by the sample 4 over a predetermined wavelength range. In simple embodiments it may be a rigid wall element.

The closing element 8 may be formed as a slide or a flap which can be closed in a vacuum-tight manner. In any case, one position of the closing element 8 must be provided in which it separates the sample chamber 2 in a vacuum-tight manner from the detector chamber 9, which is usually evacuated.

The X-ray fluorescence light entering the detector chamber 9 reaches—via a first collimator 10—via an analyzer element 11, preferably an analyzer crystal, via a second collimator 12, a detector 13 where it is received and transformed into electric signals supplied to measuring electronics not shown in the drawing.

In order to limit the field of view of the first collimator 10 for the radiation to be detected, the sample chamber 2 is provided with an aperture diaphragm 14 between the measuring position of the sample 4 and the closing element 8.

The sample chamber 2 is formed such that in the "open" state of the moveable wall element 5 direct access is possible to the sample support 3 comprising the test sample 4, to the aperture diaphragm 14 and to the primary ray filter element 7. After removal of the aperture diaphragm 14 direct access is possible to the closing element 8 and after removal of the primary ray filter element 7 to the exit window 16 of the X-ray tube 6, e.g. to enable adjustment or repair works.

The drawing shows an automatic sample changing device 17 cooperating with the moveable wall element 5, which can transport the sample 4 to be examined directly from the atmosphere surrounding the sample chamber 2 into the measuring position in the sample holder 3.

In order to shield the environment from the radiation generated during operation of the X-ray tube 6, the moveable wall element 5 is impervious to X-rays and contains usually layers, foils or plates of lead.

The X-ray fluorescence spectrometer 1 operates preferably in a wavelength-dispersive manner since in this way one can obtain better spectral resolution and sometimes also more exact measurement results as compared with an energy-dispersive embodiment.

Figure 2:
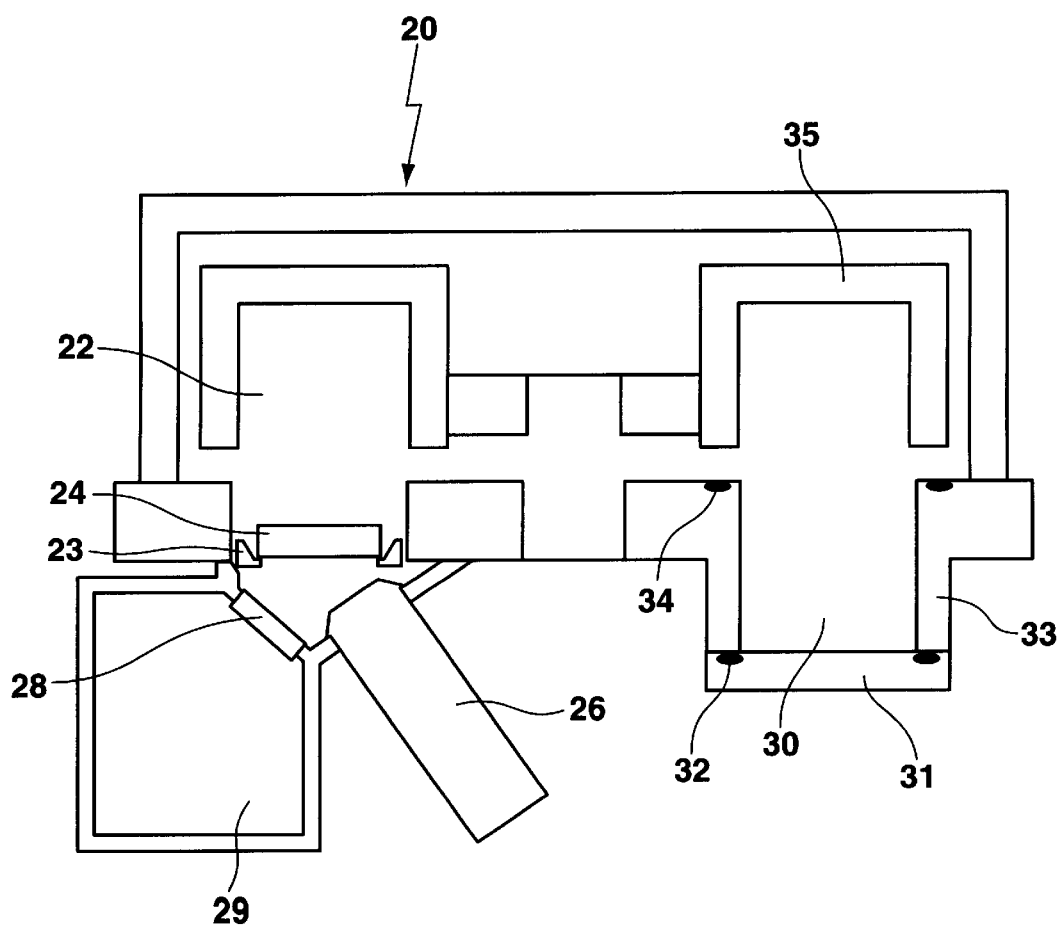
FIG. 2 shows a schematic horizontal cross section through the prior art Bruker AXS spectrometer "SRS 3400".

For comparison with the inventive construction, FIG. 2 schematically shows the set up of a conventional prior art X-ray fluorescence spectrometer 20 (Bruker AXS SRS 3400).

The known spectrometer 20 also comprises a sample chamber 22 containing a sample 24 held in its measuring position by means of a sample holder 23. An X-ray tube 26 projects into the sample chamber 22. In this case, too, a detector chamber 29 is connected to the sample chamber 22 via a closing slide 28 which can be closed in a vacuum-tight, X-ray transparent manner. The closing slide 28 is usually open and is only closed to the evacuated detector chamber 29 in case of measurements where the sample chamber 22 is flooded with gas.

Introducing the sample into the measuring position inside the sample chamber 22, however, is considerably more complicated in this known X-ray fluorescence spectrometer 20. In order to introduce the sample 24 into the apparatus, a closing element 31 on the transfer chamber 30 has to be opened and closed again after insertion of the sample 24 in a vacuum-tight manner by means of a seal 32. In this position, a first section 33 of the casing is connected in a vacuum-tight manner with a second section 35 of the casing by means of a seal 34. Subsequently, the second section 35 of the casing is separated from the first section 33 of the casing and the sample 24 is transferred through lifting, rotation by 180° and subsequent lowering into its measuring position in the sample chamber 22, which is now in communication with the transfer chamber 30.

What is claimed is:

1. An X-ray fluorescence spectrometer for the analysis of a solid or liquid sample in a measuring position on a sample holder, the sample having a maximum linear extent of one dm, the spectrometer comprising:

a sample chamber defining a first vacuum region, all portions of said first vacuum region being in constant communication with each other to maintain a substantially uniform pressure throughout said sample chamber, said sample chamber having a volume less than 10 $dm^3$;

an X-ray tube projecting into said sample chamber for irradiating the sample, said X-ray tube having an exit window forming part of a vacuum-tight wall of said sample chamber;

a movable wall element sealing an opening in said sample chamber, said movable wall element having an opened position permitting direct access to the sample in a measuring position inside said sample chamber, said movable wall element having a closed position sealing said sample chamber with respect to a surrounding atmosphere;

a detector chamber defining a second vacuum region;

a detection means disposed within said detector chamber; and a closing element disposed between said sample chamber and said detector chamber for vacuum-tight separation of said first vacuum region from said second vacuum region.

2. The X-ray fluorescence spectrometer of claim 1, wherein said movable wall element is at least one of sliding and revolving.

3. The X-ray fluorescence spectrometer of claim 2, further comprising automatic sample changing means cooperating with said movable wall element.

4. The X-ray fluorescence spectrometer of claim 3, wherein said sample changing means can transport the sample to be examined directly from the surrounding atmosphere to the measuring position inside said sample chamber.

5. The X-ray fluorescence spectrometer of claim 1, wherein said movable wall element is essentially impervious to radiation emitted by said X-ray tube.

6. The X-ray fluorescence spectrometer of claim 5, wherein said movable wall element contains lead.

7. The X-ray fluorescence spectrometer of claim 1, enabling, in said opened position of said movable wall element, direct access from the surrounding atmosphere to said exit window of said X-ray tube.

8. The X-ray fluorescence spectrometer of claim 1, enabling, in said opened position of said movable wall element, direct access from the surrounding atmosphere to a primary X-ray filter element for filtering X-rays emitted from said X-ray tube before they hit the sample.

9. The X-ray fluorescence spectrometer of claim 1, enabling, in said opened position of said movable wall element, direct access from the surrounding atmosphere to said closing element.

10. The X-ray fluorescence spectrometer of claim 1, further comprising an exchangeable aperture diaphragm located in said sample chamber between the measuring position of the sample and said closing element.

11. The X-ray fluorescent spectrometer of claim 10, enabling in said opened position of said movable wall element, direct access from the surrounding atmosphere to said aperture diaphragm.

12. The X-ray fluorescence spectrometer of claim 1, wherein said closing element is transparent to X-ray fluorescence radiation emitted by the sample of a predetermined wavelength range.

13. The X-ray fluorescent spectrometer of claim 12, wherein said closing element is a rigid wall element.

14. The X-ray fluorescent spectrometer of claim 1, wherein said closing element is formed as one of a slide and a flap which can be closed in a vacuum-tight manner.

15. The X-ray fluorescence spectrometer of claim 1, wherein said sample chamber can be evacuated.

16. The X-ray fluorescence spectrometer of claim 1, wherein said sample chamber can be flooded with at least one of nitrogen and helium.

17. The X-ray fluorescence spectrometer of claim 1, wherein said detector means is wavelength-dispersive.

18. The X-ray fluorescence spectrometer of claim 17, wherein said detection means comprises a first collimator, an analyzer element, an analyzer crystal and a second collimator.

19. The X-ray fluorescence spectrometer of claim 1, wherein said X-ray tube can illuminate at least half of a surface area of the sample in the measuring position facing said X-ray tube.

20. An X-ray fluorescence spectrometer for the analysis of a solid or liquid sample in a measuring position on a sample holder, the sample having a maximum linear extent of 1 dm, the spectrometer comprising:

a sample chamber defining a first vacuum region, all portions of said first said vacuum region being in constant communication with another to maintain a substantially uniform pressure throughout said sample chamber, said sample chamber having a volume less than 10 $dm^3$, wherein said sample chamber can be evacuated and flooded with at least one of nitrogen and helium gas;

an X-ray tube projecting into said sample chamber for irradiating the sample, said X-ray tube having an exit window forming part of a vacuum-tight wall of said sample chamber, said X-ray tube illuminating at least half of a surface area of the sample in the measuring position facing said X-ray tube;

a movable wall element sealing an opening of said sample chamber, said movable wall element having an opened position permitting direct access to the sample in the measuring position inside said sample chamber, said movable wall element having a closed position sealing said sample chamber with respect to a surrounding atmosphere;

a detector chamber defining a second vacuum region;

a wavelength-dispersive detection means disposed within said detector chamber; and a closing element disposed between said sample chamber and said detector chamber for vacuum-tight separation of said first vacuum region from said second vacuum region.

* * * * *